(12) United States Patent
Yoon et al.

(10) Patent No.: US 9,539,294 B2
(45) Date of Patent: Jan. 10, 2017

(54) **METHOD FOR PREVENTION AND TREATMENT OF *STREPTOCOCCUS PARAUBERIS* INFECTIONS**

(71) Applicant: iNtRON Biotechnology, Inc., Kyeonggi-do (KR)

(72) Inventors: Seong Jun Yoon, Seoul (KR); Soo Youn Jun, Seoul (KR); An Sung Kwon, Gwangju-si (KR); Young Jae Hur, Gwangju-si (KR); Jung Mi Kim, Gwangju-si (KR); Sang Hyeon Kang, Seoul (KR)

(73) Assignee: INTRON BIOTECHNOLOGY, INC., Kyeonggi-do (KR)

( * ) Notice: Subject to any disclaimer, the term of this patent is extended or adjusted under 35 U.S.C. 154(b) by 0 days.

(21) Appl. No.: 14/698,593

(22) Filed: Apr. 28, 2015

(65) Prior Publication Data

US 2015/0306159 A1    Oct. 29, 2015

(30) Foreign Application Priority Data

Apr. 29, 2014 (KR) .......................... 10-2014-0051211

(51) Int. Cl.
*A61K 35/76* (2015.01)
*A23K 1/00* (2006.01)
*A23K 1/17* (2006.01)
*C12N 7/00* (2006.01)

(52) U.S. Cl.
CPC .............. *A61K 35/76* (2013.01); *A23K 10/18* (2016.05); *A23K 20/195* (2016.05); *A23K 50/80* (2016.05); *C12N 7/00* (2013.01); *C12N 2795/10321* (2013.01); *C12N 2795/10332* (2013.01)

(58) Field of Classification Search
None
See application file for complete search history.

(56) References Cited

PUBLICATIONS

*Lactococcus* Bacteriophage phi 31 (GenBank Accession No. AJ292531.2).

*Primary Examiner* — Jennifer McDonald
*Assistant Examiner* — Qing Xu
(74) *Attorney, Agent, or Firm* — Foley & Lardner LLP

(57) ABSTRACT

A composition includes an isolated bacteriophage Str-PAP-1 having the ability to kill *Streptococcus parauberis* cells specifically by infecting the same, and may be used to prevent and treat *Streptococcus parauberis* infections. The bacteriophage Str-PAP-1 that is an active ingredient of the composition has the ability to kill *Streptococcus parauberis* cells and characteristically has the genome represented by nucleotide sequence of SEQ. ID. NO: 1.

21 Claims, 1 Drawing Sheet

METHOD FOR PREVENTION AND TREATMENT OF *STREPTOCOCCUS PARAUBERIS* INFECTIONS

CROSS-REFERENCE TO RELATED APPLICATIONS

The present application claims the benefit of and priority to Korean Patent Application No. 10-2014-0051211, filed Apr. 29, 2014, the entire disclosure of which is incorporated by reference herein.

SEQUENCE LISTING

The instant application contains a Sequence Listing which has been submitted electronically in ASCII format and is hereby incorporated by reference in its entirety. Said ASCII copy, created on May 28, 2015, is named 110552-0102 SL.txt and is 48,134 bytes in size.

BACKGROUND

The present application relates to a composition usable for preventing or treating *Streptococcus parauberis* infections comprising an isolated bacteriophage that is able to infect and kill *Streptococcus parauberis* cells, and a method for preventing and treating *Streptococcus parauberis* infections using the composition. More particularly, the present application relates to the bacteriophage characteristically having the genome represented by nucleotide sequence of SEQ. ID. NO: 1 that is able to kill specifically *Streptococcus parauberis* cells, a composition comprising the bacteriophage for preventing and treating *Streptococcus parauberis* infections and a method for preventing and treating *Streptococcus parauberis* infections using the composition.

The importance of aquaculture production in the fishery industry increases continuously. Because the wild fish captured are not sufficient to meet global fish demand, the supply and demand of aquaculture products are expected to increase continuously. Aquaculture production is expected to remain an important part of fishery industry.

In aquaculture production, disease outbreaks are considered to be a key constraint in the fish farming sector, resulting in significant losses. Disease outbreaks cause the economic damage and reduced productivity attributed to the increased general expense of fish culture resulted from the increase of drug use and management costs thereby. In addition, antibiotics residue has been another sensitive social issue, so the production of high quality safe aquatic products seems to be in doubt. Therefore, a method for preventing and treating the disease of cultured fish has been a major interest not just domestically, but internationally.

*Streptococcus parauberis* is well known as one of the most representative causative pathogen of streptococcosis in cultured fish. In addition to *Streptococcus parauberis, S. iniae, S. difficilis, S. shiloi*, and *Lactococcus garvieae* are also known as pathogenic bacteria that cause streptococcosis. Among them, *Streptococcus parauberis* is the most frequently reported causative pathogen of streptococcosis in fish.

In terms of external signs, a sea fish having streptococcosis shows darkened body color, exophthalmos and hyperemia, abdominal distension, and hernia. Internally, such symptoms as ascites, abdominal wall hemorrhage, and heart abscess were observed. In some cases, only gill erosion is observed without any other symptoms. Streptococcosis usually occurs in adult fish rather than a juvenile fish, indicating that economic damage is comparatively higher than other bacterial diseases.

Outbreak of streptococcosis can be influenced by several factors of deterioration of environmental conditions, inappropriate culture methods, and inappropriate feeds, etc. Streptococcosis is commonly found when water temperatures are warm, but may be common in the winter when water temperatures are low. The damage in the aquaculture production by such *Streptococcus parauberis* infections is getting bigger, so that a method to prevent the infections and also to treat the infections efficiently is urgently requested.

A variety of antibiotics have been used for the prevention or treatment of *Streptococcus parauberis* infections. However, according to the increase of antibiotic-resistant bacteria, another way of treating the infections is urgently requested. To control the infections caused by *Streptococcus parauberis*, a vaccine has been developed. However, the variety of vaccines cannot catch up with the variety of diseases. In addition, to control the multiple diseases broken at the same time, a combined control method to treat them along with a vaccine has to be prepared.

Recently, the use of bacteriophages has drawn our attention as a new way of treating bacterial infections. Particularly, the reason of our high interest in bacteriophages is because bacteriophage-based treatment is a nature-friendly method. Bacteriophages are an extremely small microorganism that infects bacteria, which is called phage in short. Once it infects bacteria, the bacteriophage is proliferated in the inside of the bacterial cell. After full proliferation, the progenies destroy the bacterial cell wall to escape from the host, suggesting that the bacteriophage has bacteria killing ability. The bacteriophage infection is characterized by high specificity, so that a certain bacteriophage infects only a specific bacterium. That is, the bacterium that can be infected by certain bacteriophage is limited, suggesting that bacteriophage can kill only a specific bacterium and cannot harm other bacteria.

Bacteriophage was first found out by an English bacteriologist Twort in 1915 when he noticed that *Micrococcus* colonies melted and became transparent by something unknown. In 1917, a French bacteriologist d'Herelle found out that *Shigella disentriae* in the filtrate of dysentery patient feces melted by something, and further studied about this phenomenon. As a result, he identified bacteriophage independently, and named it as bacteriophage which means a bacteria killer. Since then, bacteriophages specifically acting against such pathogenic bacteria as *Shigella, Salmonella typhi*, and *Vibrio cholerae* have been continuously identified.

Owing to the unique capability of bacteriophage to kill bacteria, bacteriophages have been studied and anticipated as a method to treat bacterial infections. However, after penicillin was found by Fleming, studies on bacteriophages had been only continued in some of Eastern European countries and the former Soviet Union because of the universalization of antibiotics. After the year of 2000, the merit of the conventional antibiotics faded because of the increase of antibiotic-resistant bacteria. So, bacteriophages are once again spotlighted as a new anti-bacterial agent that can replace the conventional antibiotics.

According to the recent regulation of use of antibiotics by the government, the interest on bacteriophages increases more and more.

Thus, the present inventors tried to develop a composition for preventing or treating *Streptococcus parauberis* infections by using an isolated bacteriophage that is able to kill Streptococcus parauberis cells specifically and to establish a method for preventing or treating Streptococcus parauberis infections using the composition. As a result, the present inventors secured the nucleotide sequence of the genome that can distinguish this bacteriophage from other bacteriophages and then developed a composition comprising the isolated bacteriophage as an active ingredient, and further confirmed that this composition could be efficiently used for the prevention and treatment of Streptococcus parauberis infections.

SUMMARY

It is an object of the exemplary embodiment disclosed herein to provide a novel bacteriophage that has the capability to kill Streptococcus parauberis cells specifically.

It is another object of the exemplary embodiment disclosed herein to provide a composition for preventing Streptococcus parauberis infections comprising the bacteriophage having the capability to kill Streptococcus parauberis cells by infecting Streptococcus parauberis cells, and a method for preventing Streptococcus parauberis infections using the said composition.

It is also an object of the exemplary embodiment disclosed herein to provide a composition for treating Streptococcus parauberis infections comprising the bacteriophage having the capability to kill Streptococcus parauberis cells by infecting Streptococcus parauberis cells, and a method for treating Streptococcus parauberis infections using the said composition.

It is further an object of the exemplary embodiment disclosed herein to provide a bath (immersion) treatment agent for preventing and treating Streptococcus parauberis infections using the said composition.

It is also an object of the exemplary embodiment disclosed herein to provide a feed additive for preventing and treating Streptococcus parauberis infections using the said composition.

To achieve the above objects, the exemplary embodiment disclosed herein provides a composition comprising an isolated bacteriophage that has the capability to kill Streptococcus parauberis cells by infecting the same as an active ingredient, and a method for preventing and treating Streptococcus parauberis infections by using the composition.

The isolated bacteriophage included in the composition of the exemplary embodiment disclosed herein as an active ingredient is the bacteriophage Str-PAP-1 having the DNA genome represented by nucleotide sequence of SEQ. ID. NO: 1. The bacteriophage Str-PAP-1 isolated by the present inventors was deposited at Korean Collection for Type Cultures, Korea Research Institute of Bioscience and Biotechnology in Apr. 7, 2014 (Accession No: KCTC 12568BP).

The exemplary embodiment disclosed herein also provides a bath treatment agent and a feed additive for the prevention and treatment of Streptococcus parauberis infections.

The bacteriophage Str-PAP-1 included in the composition of the invention can kill Streptococcus parauberis cells efficiently, so that it displays the preventive or therapeutic effect on streptococcosis caused by Streptococcus parauberis. Therefore, the composition of the exemplary embodiment disclosed herein can be used for the prevention and treatment of streptococcosis caused by Streptococcus parauberis. In this description, streptococcosis indicates all the symptoms accompanied by Streptococcus parauberis infections.

In this description, the term "treatment" or "treat" indicates (i) to suppress streptococcosis caused by Streptococcus parauberis; and (ii) to relieve streptococcosis caused by Streptococcus parauberis.

In this description, the term "isolation" or "isolated" indicates all the action to separate the bacteriophage by using diverse experimental techniques and to secure the characteristics that can distinguish this bacteriophage from others, and further includes the action of proliferating the bacteriophage via bioengineering techniques so as to make it useful.

The bacteriophage of the exemplary embodiment disclosed herein includes the bacteriophage Str-PAP-1 and its variants. The "variants" herein indicate the bacteriophages that have minor variations in genomic sequence or polypeptide coding genetic information but have the same genotypic and phenotypic characteristics as the bacteriophage Str-PAP-1 of the invention. The said variants include polymorphic variants as well. It is preferred for those variants to have the same or equivalent biological functions as the bacteriophage Str-PAP-1 of the invention.

The pharmaceutically acceptable carrier included in the composition of the exemplary embodiment disclosed herein is the one that is generally used for the preparation of a pharmaceutical formulation, which is exemplified by glucose, maltodextrin, lactose, dextrose, sucrose, sorbitol, mannitol, starch, acacia rubber, calcium phosphate, alginate, gelatin, calcium silcate, microcrystalline cellulose, polyvinyl pyrrolidone, cellulose, water, syrup, methylcellulose, methylhydroxybenzoate, propylhydroxybenzoate, talc, magnesium stearate, and mineral oil, but not always limited thereto. The composition of the exemplary embodiment disclosed herein can additionally include lubricants, wetting agents, sweeteners, flavors, emulsifiers, suspending agents, and preservatives, in addition to the above ingredients.

In the composition of the exemplary embodiment disclosed herein, the bacteriophage Str-PAP-1 or the variants thereof are included as an active ingredient. At this time, the bacteriophage Str-PAP-1 or the variants thereof are preferably included at the concentration of $1 \times 10^1$ pfu/mL~$1 \times 10^{30}$ pfu/mL or $1 \times 10^1$ pfu/g~$1 \times 10^{30}$ pfu/g, and more preferably at the concentration of $1 \times 10^4$ pfu/mL~$1 \times 10^{15}$ pfu/mL or $1 \times 10^4$ pfu/g~$1 \times 10^{15}$ pfu/g.

The composition of the exemplary embodiment disclosed herein can be formulated by the method that can be performed by those in the art by using a pharmaceutically acceptable carrier and/or excipient in the form of unit dose or in a multi-dose container. The formulation can be in the form of solution, suspension or emulsion in oil or water-soluble medium, extract, powder, granule, tablet or capsule. At this time, a dispersing agent or a stabilizer can be additionally included.

The composition of the exemplary embodiment disclosed herein can be prepared as a bath treatment agent or a feed additive according to the purpose of use, but not always limited thereto.

Advantageous Effect

The composition of the exemplary embodiment disclosed herein and the method for preventing and treating Streptococcus parauberis infections using the composition has the advantage of high specificity to Streptococcus parauberis, compared with the conventional chemical or synthetic antibiotics. That means, the composition of the exemplary embodiment disclosed herein can be used for preventing or treating Streptococcus parauberis specifically without affecting other useful bacteria in vivo, and accordingly has less side effects. In general, when chemical materials such as antibiotics are used, the general beneficial bacteria are also damaged to weaken immunity in animals with carrying various side effects. In the meantime, the composition of the exemplary embodiment disclosed herein uses the isolated bacteriophage as an active ingredient, so that it is very nature-friendly.

BRIEF DESCRIPTION OF THE DRAWINGS

The application of the preferred embodiments is best understood with reference to the accompanying drawings, wherein.

DETAILED DESCRIPTION

Figure 1:
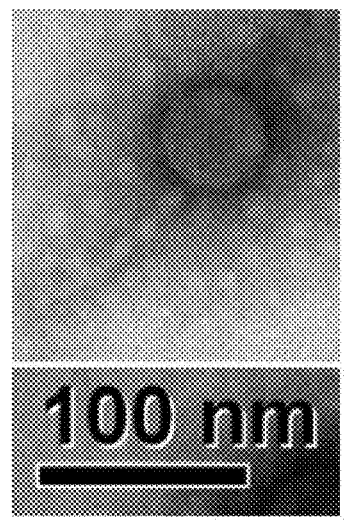
FIG. 1 is an electron micrograph showing the bacteriophage Str-PAP-1.

Practical and presently preferred embodiments are illustrative as shown in the following Examples. It is to be understood that the present disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

However, it will be appreciated that those skilled in the art, on consideration of this disclosure, may make modifications and improvements within the spirit and scope of the present invention. The detailed description of the present disclosure is divided into various sections only for the reader's convenience and disclosure found in any section may be combined with that in another section. Unless defined otherwise, all technical and scientific terms used herein have the same meaning as commonly understood by one of ordinary skill in the art to which the present disclosure belongs.

The following Examples are intended to further illustrate certain embodiments of the disclosure and are not intended to limit its scope.

Example 1

Isolation of Bacteriophage Capable of Killing *Streptococcus parauberis* Cells

Samples were collected from the nature or animals to screen the bacteriophage having the capability to kill *Streptococcus parauberis* cells. The strains of *Streptococcus parauberis* used for the bacteriophage isolation herein were the one that had been already separated by the present inventors and identified as *Streptococcus parauberis*.

The isolation process of the bacteriophage is described in more detail hereinafter. The collected sample was added to the TSB (Tryptic Soy Broth) medium (casein digest, 17 g/L; soybean digest, 3 g/L; dextrose, 2.5 g/L; NaCl, 5 g/L; dipotassium phosphate, 2.5 g/L) inoculated with *Streptococcus parauberis* culture at the ratio of 1/1000, followed by shaking culture at 30° C. for overnight. Upon completion of the culture, centrifugation was performed at 8,000 rpm for 20 minutes and supernatant was collected. The recovered supernatant was filtered by using a 0.45 μm filter. The obtained filtrate was screened by spot assay to investigate whether or not the bacteriophage that can kill *Streptococcus parauberis* cells was included therein.

Spot assay was performed as follows; TSB medium was inoculated with *Streptococcus parauberis* culture at the ratio of 1/1000, followed by shaking culture at 30° C. overnight. 3 mL ($OD_{600}$=2.0) of the *Streptococcus parauberis* culture broth prepared above was spread on the TSA (Tryptic Soy Agar; casein digest, 15 g/L; soybean digest, 5 g/L; NaCl, 5 g/L; agar, 15 g/L) plate. The plate stood in a clean bench for 20 minutes to dry the culture broth.

After the medium was dried, 10 μl of the prepared filtrate was dropped on the plate on which *Streptococcus parauberis* had been spread. The plate stood for about 20 minutes to dry the medium, followed by standing-culture at 30° C. for a day. The next day, the plate was observed to see whether or not a clear zone was generated on the spot where the filtrate was dropped. If a clear zone was generated where the filtrate was dropped, it could be judged that the bacteriophage that could kill *Streptococcus parauberis* cells was included in the filtrate. Through the above procedure, the filtrate containing the bacteriophage having the capability to kill *Streptococcus parauberis* cells could be obtained.

Then, the bacteriophage was isolated from the filtrate confirmed above to have the bacteriophage capable of killing *Streptococcus parauberis* cells. The conventional plaque assay was used for the bacteriophage isolation. Particularly, a plaque formed in the course of the plaque assay was picked up by using a blade, which was then added to phage buffer (10 mM Tris-HCl (pH7.5), 10 mM MgSO4, NaCl 4 g/L). The buffer stood for 4 hours. Centrifugation was performed at 5,000 rpm for 15 minutes to obtain supernatant. The obtained supernatant was filtered by using a 0.45 μm filter. The obtained supernatant was used for plaque assay again. In general, the pure bacteriophage isolation is not completed by one-time process, so the above procedure was repeated. At least 5 times of repeated procedure, the solution containing the pure bacteriophage was obtained. The procedure for the isolation of the pure bacteriophage is generally repeated until the generated plaques become similar in sizes and morphologies. The final pure bacteriophage isolation was confirmed by the observation under electron microscope. Until the pure bacteriophage isolation was confirmed under electron microscope, the above process was repeated. The observation under electron microscope was performed by the conventional method. Briefly, the solution containing the pure bacteriophage was loaded on copper grid, followed by negative staining with 2% uranyl acetate. After drying thereof, the morphology was observed under transmission electron microscope.

The solution containing the pure bacteriophage confirmed above proceeded to purification. *Streptococcus parauberis* culture broth was added to the solution containing the pure bacteriophage at the volume of 1/10 of the total volume of the bacteriophage solution, followed by culture for 4~5 hours. Upon completion of the culture, centrifugation was performed at 8,000 rpm for 20 minutes to obtain supernatant. The said procedure was repeated 5 times to obtain a solution containing enough numbers of the bacteriophage. The supernatant obtained from the final centrifugation was filtered by a 0.45 μm filter, followed by the conventional polyethylene glycol (PEG) precipitation. Particularly, PEG and NaCl were added to 100 mL of the filtrate (10% PEG 8000/1 M NaCl), which stood at 4° C. for overnight. Centrifugation was performed at 8,000 rpm for 30 minutes to obtain the bacteriophage precipitate. The obtained bacteriophage precipitate was resuspended in 5 mL of buffer (10 mM Tris-HCl, 10 mM MgSO4, 0.1% Gelatin, pH 8.0). This solution was called the bacteriophage suspension or bacteriophage solution.

As a result, the purified pure bacteriophage was obtained, which was named as the bacteriophage Str-PAP-1 and then deposited at Korean Collection for Type Cultures, Korea Research Institute of Bioscience and Biotechnology in Apr. 7, 2014 (Accession No: KCTC 12568BP). The electron micrograph of the bacteriophage Str-PAP-1 is presented in FIG. 1. From the morphological observation, the bacteriophage Str-PAP-1 was identified as belonging to the family Siphoviridae.

Example 2

Separation of the Bacteriophage Str-PAP-1 Genome and Sequencing Thereof

The genome of the bacteriophage Str-PAP-1 was separated as follows. The genome was separated from the bacteriophage suspension obtained in Example 1. First, in order to eliminate DNA and RNA of *Streptococcus parauberis* host bacterial cells included in the suspension, DNase I and RNase A were added 200 U each to 10 mL of the bacteriophage suspension, which stood at 37° C. for 30 minutes. 30 minutes later, to remove the DNase I and RNase A activity, 500 μl of 0.5 M ethylenediaminetetraacetic acid (EDTA) was added thereto, which stood for 10 minutes. The suspension stood at 65° C. for 10 minutes and then added with 100 μl of proteinase K (20 mg/mL) to break the outer wall of the bacteriophage, followed by incubation at 37° C. for 20 minutes. 500 μl of 10% sodium dodecyl sulfate (SDS) was added thereto, followed by incubation at 65° C. for 1 hour. 10 ml of the mixture of phenol:chloroform:isoamyl-alcohol (25:24:1) was added thereto, followed by mixing well. The mixture was centrifuged at 13,000 rpm for 15 minutes to separate each layer. The upper layer was obtained, to which isopropyl alcohol was added at the volume of 1.5 times the volume of the upper layer, followed by centrifugation at 13,000 rpm for 10 minutes to precipitate the genome of bacteriophage. After collecting the precipitate, 70% ethanol was added to the precipitate, followed by centrifugation at 13,000 rpm for 10 minutes to wash the precipitate. The washed precipitate was vacuum-dried and then dissolved in 100 μl of water. The said process was repeated to obtain the bacteriophage Str-PAP-1 genome in a large scale.

The nucleotide sequence of the genome of the bacteriophage Str-PAP-1 obtained above was analyzed by Next Generation Sequencing (NGS) at National Instrumentation Center for Environmental Management, Seoul National University. Briefly, DNA fragment was fixed on the slide, followed by bridge amplification to form DNA fragment cluster. Then, SBS (Sequence by Synthesis), that was a nucleotide synthesis reaction, was performed by using the cluster as a template along with four different fluorescent-labeled nucleotides. This method is unique by the following characteristics: wherein DNA sequence is not amplified in a reaction solution like other methods but amplified on the slide where DNA is fixed with DNA bending to form sequence clusters. The formed cluster proceeded to sequencing group by group, and the obtained results are converted into each read sequence information, followed by examination. A contig map was prepared by using the obtained gene sequence by the conventional method. The nucleotide sequence of the total genome in the size of 36,595 bp was analyzed by primer walking. The total genomic sequence of the bacteriophage Str-PAP-1 was represented by nucleotide sequence of SEQ. ID. NO: 1.

Similarity of the genomic sequence of the bacteriophage Str-PAP-1 obtained above with the previously reported bacteriophage genome sequences was investigated by using BLAST. As a result, the genomic sequence of the bacteriophage Str-PAP-1 had a similarity with only sequence of *Lactococcus* bacteriophage phi31 (GenBank Accession No. AJ292531.2), but the similarity is very low (1%). It suggests that the bacteriophage Str-PAP-1 as disclosed herein was clearly distinguished from the previously reported bacteriophages.

From the above results, it was confirmed that the bacteriophage Str-PAP-1 was a novel bacteriophage that was completely different from the previously reported bacteriophages.

Example 3

Investigation of *Streptococcus parauberis* Killing Ability of the Bacteriophage Str-PAP-1

Figure 2:
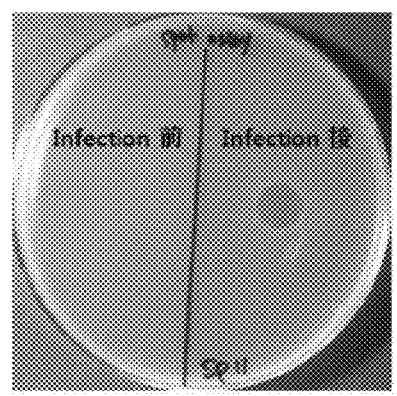
FIG. 2 is a photograph of a spot assay illustrating the capability of the bacteriophage Str-PAP-1 to kill *Streptococcus parauberis* cells. The photograph shows *Streptococcus parauberis*-infected culture broth spread on a tryptic soy agar (TSA) plate. The vertical line divides the plate into two zones of infection. The left zone of infection was not treated with Str-PAP-1. The right zone of infection was treated with a 10 μL drop of a solution containing Str-PAP-1. A clear zone appeared in the right zone of infection where the solution containing Str-PAP-1 was dropped.

The *Streptococcus parauberis* killing ability of the isolated bacteriophage Str-PAP-1 was investigated. To do so, the formation of clear zone was first observed by the spot assay in the same manner as described in Example 1. Those *Streptococcus parauberis* bacteria strains used for the killing ability investigation totaled 55 strains which were separated and identified as *Streptococcus parauberis* strains previously by the present inventors. The bacteriophage Str-PAP-1 demonstrated the ability to kill 35 strains of those *Streptococcus parauberis* bacteria. The representative results of this investigation are presented in FIG. 2. In the meantime, the activity of the bacteriophage Str-PAP-1 to kill *Edwardsiella tarda*, *Vibrio anguillarum*, *Vibrio ichthyoenteri*, *Lactococcus garvieae*, and *Streptococcus iniae* was also investigated. As a result, the bacteriophage Str-PAP-1 did not have the activity of killing these microorganisms.

Therefore, the results above indicate that the bacteriophage Str-PAP-1 of the present invention can be efficiently used as an active ingredient of a composition for preventing and treating *Streptococcus parauberis* infections.

Example 4

Preventive Effect of Bacteriophage Str-PAP-1 on *Streptococcus parauberis* Infections 100 μl of the bacteriophage Str-PAP-1 solution (1×109 pfu/mL) was added to a tube containing 9 mL of TSB. To another tube containing 9 mL of TSB, 100 μl of TSB was added. *Streptococcus parauberis* culture was added to each tube to prepare bacterial suspensions of $OD_{600}=0.5$. Then, the tubes were transferred in a 30° C. incubator, followed by shaking-culture, during which the growth of *Streptococcus parauberis* was observed. As presented in Table 1, the growth of *Streptococcus parauberis* was inhibited in the tube added with the bacteriophage Str-PAP-1 solution, while the growth of *Streptococcus parauberis* was not inhibited in the tube not added with the bacteriophage Str-PAP-1 solution.

TABLE 1

Inhibition of *Streptococcus parauberis* growth

| | OD600 | | |
|---|---|---|---|
| | 0 min. | 15 min. | 60 min. |
| (−) bacteriophage solution | 0.5 | 0.62 | 0.94 |
| (+) bacteriophage solution | 0.5 | 0.60 | 0.32 |

The above results indicate that the bacteriophage Str-PAP-1 not only inhibits the growth of *Streptococcus parauberis* cells but also can kill the bacteria. Therefore, the bacteriophage Str-PAP-1 can be used as an active ingredient of a composition for preventing *Streptococcus parauberis* infections.

Example 5

Therapeutic Effect of Bacteriophage Str-PAP-1 on *Streptococcus parauberis* Infections Therapeutic effect of the bacteriophage Str-PAP-1 on the olive flounder having *Streptococcus parauberis* infection was investigated. Particularly, two groups of juvenile olive flounder (10 fish per group, body length 6~9 cm) at 4 months old were prepared, which were cultured separately in different water tanks for 14 days. Surrounding environment of the water tanks was controlled. The temperature and humidity in the laboratory where the water tanks stayed were also controlled. On the 7th day of the experiment, *Streptococcus parauberis* suspension (100 μl) was administered to the fish via intraperitoneal injection. The *Streptococcus parauberis* suspension was prepared as follows: *Streptococcus parauberis* was cultured in TSB medium at 30° C. for 18 hours. The bacterial cells were collected, which were prepared at the concentration of 1×108 CFU/mL by using saline (pH 7.2). From the next day of the *Streptococcus parauberis* challenge, the fish were intraperitoneally administered with 1×108 pfu/rite of the bacteriophage Str-PAP-1 (100 μl) once a day. The control group fish (bacteriophage solution not-treated) were not treated with anything. Feeds were equally provided to both the control and experimental groups. After the challenge of *Streptococcus parauberis*, all the test fish were examined to see if streptococcosis was developed or not. The outbreak of streptococcosis was assessed by monitoring the extent of darkened body color. The measurement of dark coloration score (0: normal, 1: light dark coloration, 2: heavy dark coloration) was performed. The results are shown in Table 2.

TABLE 2

Dark coloration score

| | Days after the *Streptococcus parauberis* challenge | | | | | | |
|---|---|---|---|---|---|---|---|
| | 0 | 1 | 2 | 3 | 4 | 5 | 6 |
| Control group (−bacteriophage solution) | 1.0 | 1.5 | 1.5 | 1.25 | 1.1 | 1.25 | 1.25 |
| Experimental group (+bacteriophage solution) | 1.0 | 0.5 | 0.25 | 0.25 | 0.1 | 0 | 0 |

From the above results, it was confirmed that the bacteriophage Str-PAP-1 as disclosed herein could be very efficient to treat *Streptococcus parauberis* infections.

Example 6

Preparation of Feed Additives and Feeds

Feed additives were prepared by adding the bacteriophage Str-PAP-1 solution at the concentration of 1×109 pfu/g to the feed additives. The preparation method thereof was as follows: Maltodextrin (40 weight %) and trehalose (10 weight %) were added to the bacteriophage solution. After mixing well, the mixture was freeze-dried. Lastly, the dried mixture was ground into fine powders. The drying process above can be replaced with vacuum-drying, drying at warm temperature, or drying at room temperature. To prepare the control feed additive for comparison, feed additive that did not contain the bacteriophage but contained buffer (10 mM Tris-HCl, 10 mM MgSO4, 0.1% Gelatin, pH 8.0) were prepared.

The above two kinds of feed additives were mixed with live fish meals at the volume of 250 times the volume of feed additive, resulting in two kinds of final feeds.

Example 7

Preparation of a Bath Treatment Agent

A bath treatment agent containing $1×10^9$ pfu/mL of bacteriophage Str-PAP-1 was prepared. The preparation method was as follows: $1×10^9$ pfu of the bacteriophage Str-PAP-1 was added to 1 mL of buffer, which was well mixed. To prepare the control bath treatment agent, the buffer itself that was the same as the one used for the mixture of the bacteriophage solution was prepared.

The prepared two kinds of bath treatment agents were diluted with water at the ratio of 1:1,000, resulting in the final bath treatment agents for the experiment.

Example 8

Effect on Fish Farming

The effect of the feeds and the bath treatment agents prepared in Example 6 and Example 7 on olive flounder farming was investigated. Particularly, the investigation was focused on mortality. A total of 20 fish were split into two groups, 10 fish for each groups, which proceeded to the following experiment (group A; fed with feeds, group B; treated with bath treatment agents). Each group was divided by two sub-groups again, group of 5 fish each (sub-group-①: treated with the bacteriophage Str-PAP-1, sub-group-②: not-treated with the bacteriophage Str-PAP-1). The fish used for this experiment were the juvenile olive flounder at 4 months old. Each sub-group fish were cultured in separate water tanks placed at a sufficient distance from each other. Each sub-group was distinguished and named as shown in Table 3.

TABLE 3

Sub-groups of feeding experiment

| | Sub-group | |
|---|---|---|
| | Treated with the bacteriophage Str-PAP-1 | Not-treated with the bacteriophage Str-PAP-1 |
| Fed with feeds | A-① | A-② |
| Treated with bath treatment agents | B-① | B-② |

Feeds were provided according to the conventional feed supply method as presented in Table 3 with the feeds prepared in Example 6. The treatment of bath treatment agents was also performed by the conventional method according to Table 3 with the bath treatment agents prepared in Example 7. The results are shown in Table 4.

TABLE 4

| Group | Mortality (%) |
|---|---|
| A-① | 0 |
| A-② | 20 |
| B-① | 0 |
| B-② | 40 |

The above results indicate that the feeds prepared by the exemplary embodiment disclosed herein and the bath treatment agents prepared according to the exemplary embodiment disclosed herein are effective in reducing fish mortality. Therefore, it can be concluded that the composition of the exemplary embodiment disclosed herein can be efficiently applied for the improvement of productivity of fish farming.

Those skilled in the art will appreciate that the conceptions and specific embodiments disclosed in the foregoing description may be readily utilized as a basis for modifying or designing other embodiments for carrying out the same purposes of the exemplary embodiment disclosed herein. Those skilled in the art will also appreciate that such equivalent embodiments do not depart from the spirit and scope of the invention as set forth in the appended Claims.

What is claimed is:

1. A method for treating or decreasing the probability for developing *Streptococcus parauberis* infections in an animal in need thereof, comprising: administering to the animal a therapeutically effective amount of a composition comprising bacteriophage Str-PAP-1 having Accession No. KCTC 12568BP, wherein the bacteriophage comprises the sequence of SEQ ID NO: 1.

2. The method of claim 1, wherein the animal is a fish.

3. The method of claim 2, wherein the fish is in an aquaculture environment.

4. The method of claim 3, wherein the administering comprises providing the composition to the aquaculture environment.

5. The method of claim 4, wherein the composition is formulated as a fish feed or fish feed additive.

6. The method of claim 5, wherein the composition is formulated as a fish feed additive and comprises, in addition to the bacteriophage Str-PAP-1, one or more compounds selected from the group consisting of: maltodextrin and trehalose.

7. The method of claim 6, wherein the fish feed additive is freeze-dried.

8. The method of claim 5, wherein the composition is formulated as a fish feed and comprises, in addition to the bacteriophage Str-PAP-1, fish meal.

9. The method of claim 4, wherein the composition is formulated as a bath treatment agent.

10. The method of claim 9, wherein the bath treatment agent comprises, in addition to the bacteriophage Str-PAP-1 comprising the sequence of SEQ ID NO: 1, a buffer.

11. The method of claim 3, wherein the administering comprises injecting the fish with the composition.

12. The method of claim 4, wherein the fish exhibits symptoms of *Streptococcus parauberis* infections prior to the administering.

13. The method of claim 12, wherein the symptoms include one or more selected from the group consisting of: darkened body color, exophthalmos, hyperemia, abdominal distension, hernia, and gill erosion.

14. The method of claim 4, wherein the administering comprises providing the composition to the aquaculture environment prior to the fish showing symptoms of *Streptococcus parauberis* infections.

15. The method of claim 14, wherein the composition is formulated as a fish feed or fish feed additive.

16. The method of claim 15, wherein the composition is formulated as a fish feed additive and comprises, in addition to the bacteriophage Str-PAP-1, one or more compounds selected from the group consisting of: maltodextrin and trehalose.

17. The method of claim 16, wherein the fish feed additive is freeze-dried.

18. The method of claim 15, wherein the composition is formulated as a fish feed and comprises, in addition to the bacteriophage Str-PAP-1, fish meal.

19. The method of claim 14, wherein the composition is formulated as a bath treatment agent.

20. The method of claim 19, wherein the bath treatment agent comprises, in addition to the bacteriophage Str-PAP-1 comprising the sequence of SEQ ID NO: 1, a buffer.

21. The method of claim 3, wherein the administering comprises injecting the fish with the composition prior to the fish showing symptoms of *Streptococcus parauberis* infections.

* * * * *

SEQUENCE LISTING

```
<160> NUMBER OF SEQ ID NOS: 1

<210> SEQ ID NO 1
<211> LENGTH: 36595
<212> TYPE: DNA
<213> ORGANISM: Unknown
<220> FEATURE:
<223> OTHER INFORMATION: Description of Unknown: Bacteriophage Str-PAP-1

<400> SEQUENCE: 1
atatttatat    atttattatt    attattaatt    aatagaatat    agagttaact    attaacctta        60
acttgtctaa    ttactgatat    ataagatttt    taaacagtta    agggttatca    tttttcactt       120
aactaaacta    ttaaccatta    accttgatat    aacatgtaac    tggcttttc     ggatcgtttt       180 cattgtgcca    tgaaaaaact    cctaattctg    ttggtgtatc    tacgctaggc    ataaatccaa       240
ttggtttagc    aactttcttt    tcccactctc    ctgttaaaaa    tgtaggcaat    tgcttttcaa       300
acttaaattt    atttaacgct    acaatcccag    aatctttgca    ccatgcttta    tacaaccacc       360
acagaaattt    actaggtagt    ctctttgatt    caaatttagg    aaaccattca    ttgacgaatg       420
ctttaactgt    gtcatttgat    tctttaaatt    cttctaactg    tactttagtt    gctgatggtt       480
cattaaactt    attaaaattg    atttcaagag    cttttttttaa   aacatactct    ctaacatctt       540
ccctataaat    atagtcatct    ttaatcgccc    aattatcttc    tttaggtgaa    aatgtttttc       600
taaaaggtat    aattgtaaat    cgtcgataag    taccgtttga    tttattcttg    aatcgaggca       660
attcatttgt    tgattgaatg    actgttttc     taaagatagt    tgtataaggt    tgtttattct       720
tctcctctac    taatactggt    tcaccagtaa    cgaccgaatt    gaagttagat    gattcgtcta       780
catatatacc    agcttgcaca    tcgtcaccga    taattactgt    tttaccttca    atcattgata       840
aggcgaatcg    ttctgaaaat    tggttaagct    ttaatgttgc    aatgtttttt    aaaccaatta       900
cattagttat    aagttgctga    acagtacctt    taccgtcgtt    tccttcacca    acaaaccaaa       960
ttgatttgcg    gtaagaataa    tttccattta    atgatgctga    tatgacttgc    catagtaaat      1020
caactaattc    ttcgtcattt    tccattaagt    ctaataacca    actatcgaca    tcccaaccat      1080
```

-continued

```
ttatatttgg cgacttagcg aatgcatcgt attctgtcgc aattgtcgaa aatgccacaa      1140
attgatgagt aaaacctaaa agtttttgtt ctttttttgtc atagataccg tttttcacta      1200
agataaaccg ttttggattt ttaaaatcac caattgaaaa attagaggag aatccatcat      1260
atttatgaat cctattattt gaagaaagca taaataagac attttttagct ttttgttcgt      1320 taaaggtagg ttctaacaac ctaattactt tataggcaaa tgatgggtct tgtgataat       1380 atccgttatc aggatcataa acggcaaccc tcccattgga taatgtgata atgtaaagta      1440
ggtattccat accttgagat actgctaatt catttaatgt tgttcgtttt gtatcttttt      1500
cttgcgcagt cccatcttca tttacttttg agttagcttt ttcaagccat ctatcgcgaa      1560
aattttttgc gcctaatttg atttcttttcc aatcgttagg cctttgctca tatatatcga     1620
ttattttatt ttcatattct gctttaatag cttgtatatt aactgccact tcttctatca      1680
agctcctttc tcaacatgct ctcatatgtt gcatcaactt cgttttctgg caatggattt      1740
ggtgtgtaat gattagcaag caatgccaac ttatatactg cttcttcgtc aacacctctg      1800
agcaatagtc cgcctattag acttgcaagt gaattgtttc taccaccagc atcccctaga      1860
ccaaagacaa ttttttcaaa taatttagca gtctgactac tgtatccact attacctta       1920 ctactgaaat cccttgcaac cgttttttctt gtatgaccaa tcaattcaat caattcaatt     1980
ggcgattctg cgaattttcc gccttcaagt gaattttctt tatcccatac ataactgcca      2040
ttcgtagtgt tagatggcgc aactaagaca taattgttgt cattagcttt gatatcgaca      2100
ccgtctaaga aaccaacact ctggttaatt gatacacctt taggtttctt aagaaaaata      2160
tgtctacccc cagtaggggt gatggcttga gttgttctg gaataaggtc tttaccttcc       2220
caattattaa aactttcaaa gccatcaata tcaccatgaa catctatgtc aattacaaag      2280 aagtatctg tccttactgc aatatttgca tcaggatttt ctttccataa taatttgatt       2340
tcatgttcag taaacgattt atttttaaat tttgttagtg gtcgtttact ttttttatca      2400
attggaatga cagaaaatcc gttcttctga taatgcagtg cataatctac cattcctgta     2460
atcatattag aatggtaagc catcttcgat tgattttga ttaggaatct tgtcagctaa      2520
ttgtgatgat tccattgact taatgttcaa tcgattcgtt actttacctt gatattcatt    2580 atcttcatt ttaactgtta cttttaatgc tttcccgcga atctgatcta agaaatcttt      2640
ttctgattca attactgctg atggtggaaa ttcaattgct ttagcatatt gttgtaaacg     2700
gaactctaat ggcttacctt ctgcttttga ataccagatg cggtcgaaaa ttaattgatt    2760
gtgaaattct tgtttgaaat catcacggat ctttaggcgg atatctaaga agtctgatcc    2820
gtttggtgtt gctgactgtt cagcagtatc tacaaatact tcataagttc cgtctgtgat    2880
tgatgcgaat tttttttgctt ttgaataatc tactgtgaat aatgcataa ttttatctcc    2940 aaatttcttt ttcttgttgt ttatagtaaa cccacccttt tttgtaattg tggataagtg    3000
cgaacgcttg taattctggt aatgtttgac attgtcgcca attcttaccg tatttttaa     3060 ctttagaaaa aactgcatag tctcttggac tcatttctac attttttccg tttaattcaa    3120
tctcgatgat ttcatcaact ctgactagtt caccgttaac ttttttcatt tctacctttt    3180
taggctctgg tttcaattcc tcaccacagt atggacagca cccatttact atatctgttg    3240
agaagaaagc accataacat ttaggacatt ctcttgtagc tggtgaatcg tctttatctt   3300
ttgatttttt cttttaccct tcaagaatcc aattcctatc ttgattaggg aaaccgtgga   3360
ttttccaatt accgacgtga tcaattaaga tagcttcctt cccatctctt ggattcaatg   3420
cgcgcattgc gaattgtaag tacaatgaca atgaggttgt aggtcgtaac ataatgcata   3480
```

```
catcaacatt tggtaagtct attccctctg taaaaaggtt tacattcacc attattagta    3540
agtccccatt tctaaagtct ttcatagctt tatctctaat ttctttaggt gtactaccat    3600
gtattacagc tgatgaataa cctctctcag aaaatactgt tgctatttct gttgctttta    3660
ctacagaact tgcataaacg attgcttgtt tcccttagc taaatcctca taatgtgtga    3720
catagtcacc gttaaccatt ttccagctat ctaatgattc atcaattgat ttaactgtgt    3780
aatcaccgtg tgatttttta agtttttctt tatcaatcaa ttcaagtgaa taatatcgat    3840
attttgaaat attgccttgg tcttgcaacc attttatgga tttacctacg actaaatcat    3900
cagccatatc tttaaaccca gaaccatcta gcctaattgg cgtacctgta aaaaataaat    3960
gataagcttt atcaaagtaa ttcaatattt tttgatactg ttttgctttg atatgatgcg    4020
cttcatccac taaaatgatt tctggtggtg gtaggttttc taattttcta actagacttc    4080
ctacagttcc tattgttaat aagtctgtat taacaccatt acgattaaaa gtttctttaa    4140
cttgatcgtt tatttcttta cgatgactga aaaataatac atgattccct tgtctgtag    4200 caccttagc aatatgagcc attacaactg tcttaccgct tcgaggaggt gactgaacca    4260
ttatgcgacg attaccattt agaattgatt gccctatgtt agctactaat tcttcttgat    4320
aatctcttaa attaattatt taaatcacct cacttgctta ggggtttcga tgattttctt    4380
aatatcccaa cctctatta atcgagtatt gaaagtcgag taagaaagac caattatttt    4440
agaccattga gccattgtat gagtctcccc ttcgtaggtt aaaaatctgt ttctagttgt    4500
gttgttgttt tgaacaactc gatcaaccca tctacagttt tctggggcat aatcactaga    4560
aacattaatt ctatctaaag ttaattcact actatatcca tgttctattg accaagatct    4620
aaaaaccaaa taattatgtt tccaatcttc gcatacgcta atgccttttc caccataata    4680
tttgtagttc ttagcattag tatcacggca tctttgattc atagctatcc atatactata    4740
aaggcgttct ttttttgcaa atccatgctt cattcacttt cacctccaaa attaaacaaa    4800
tcttcaatct tacaagcggt tcttccgtcc aatcgattct tggcataagt gccttcacta    4860
ccttcaagaa ttaatccacg agaacctgtt tttgcattga ctatgatgcg accgacaaca    4920
tcggtcaaac ctaataactg gtctaaaaca gaatctctaa tacgtggtac atattgagtg    4980
ataatttgtc ctgtttctag attcaggtct tgtgtagctt cccaagcggt tacgtagatg    5040
ttgattggtt taaatagat agttgttaac actcttaaga agtaattagt ccattgattg    5100
taatgttgca attcgttgct gataccattt ttagacttac gaccttgttc gataaaccag    5160
tcagattgta ggcttgatac gttatcaatg actaagttat cgtattgttc tagcacttca    5220
tcaacttctt ttaaaaggt attgatgtca tctgacggat gctctctgtc aaatgatatt    5280
gctccatcat catcaatcgt tcgaacatca acatttggaa taccttccaa aactttgtgt    5340
gaattatcaa gtgataatac taatgtatt cctttaact gtttgataag tgacgtctta    5400
cctagtccag cttccccata gataagtatt ctccaattgt tcgtgcgctg taaatctgtc    5460
gctttagtta tcttcaatgt ctaatccctc cacataatca tgagtagcat tcctataatc    5520
aaagtcgttg cgctgttgtc tgtgtttttc ttcaaacatt tcgtctacga attttctatc    5580
taaatgctcc gaatattcgt ttgctaaatt atctgcaaaa tcgttcatcc gtctatttat    5640
ttcattctca attttagtat cgaataaatc aattttgtcg gatgttatat ctccatgttt    5700
gcagttataa ctcggtacta tttgaatttt tccgaaactt gtcatgtatg ttctataatt    5760
tttcaatcgt atgccctcgc ttgccacgtt actgttgggt catcttcttc gcagtaagga    5820
```

```
caatttaaat ctctgtaatc agaaatgttt tcccaagcct taccgcaatt tgtgcaataa    5880
tattctctaa ctatcaatat gattcctttc tttatagtcg ttaacaacaa tatcgatatt    5940
gtataaatca tttgtcatat cttggttttc tttacttaaa aaaccatttt cttgttctaa    6000
ctctaaattt ctgtctagtg cttcttttag atccttttcc aatttcgctt ttttctaact    6060
tcaattcata ctcacgatga atcaagtctt gcaaatcaac aatataatct tcgtttggaa    6120
ttttagagtc acccattaaa taagcaagag ttacattaaa gtagtttgcg acacgactcc    6180
aaaatgcatc gttatgcatt ctaggttggt atacctcgta agcttttatt tcttgtttag    6240
caatgtataa acctttttct tttaacgctt ctgataactc ttcttgagtc aatccttttt    6300
cttgtcgtag ttgtttaagt ctgttcattt aaaacacctt cttattaagc ttttctttag    6360
cctctaattt agcttttga atttatctt catatttaca aattgcttca agattaaatt      6420
caatgaaatt tgtaacaact tcatttagta attcatcttt tgaagttcca ttcattttag    6480
ctaatacttc tacctgttct ttttgtagtt cagtaacttt tgctcttaca aatgaaacac    6540
ctgcgtatct atttggttta taaataccgc tcattcaaca tctcccatca ttgcatcata    6600
tttttcagca ttatgttccc atccattgtt ttggatagtc cactcttgtt tttgttcttc    6660
ttcttgtttt gtaaaagcc aattaaaaaa tttcatttgt tcatactcct taaaaatcgt     6720
tggacgtctt gcaaatcgta agtgtacttg ccacctttta cttttggtg gtatctaaat    6780 ttacctttgt cacgccaatt ttctaaagta gttctacccc atccagttat tgtttggagt    6840
tctttaatgc tgacccaatc aacttgtcta cgttgtattg ctaattcttc tgcaatcaga    6900
gcctttaatt ctgacctgct aattgtgata acatcatcca ttgattaata cctctctttc    6960
tggtataatt aaataactta atatttgtgt gagtccgact gctatcggac tttttgttg    7020 tcattgaatc cgtccagact gttgaataac tgctccataa tatggatttc gtttggggt    7080 ttcaactttc tctttagctt caattgtgat tgtgttgtct gacttaatta gtgtaatcag    7140
caaaggtgat aatattgcta ttacagtcag actttgtgcg attgttagct ccatgtgagt    7200
tcctttctag tttacgcttt gtgtagtgtt gtcgataaaa atttcgctaa tgcttttatg    7260
aaagaaatta gcaattttga acatttctga tgatgagaaa tcagtcctac caagttcttt    7320
gtttcggtaa gaaactgatg ttttccctat tacatcagcc attttttctt gagaaatatc    7380
attttgtttt ctcaattgat acaatacaat ttgcatttgt cccaaattat tctccttct     7440 gattttagt tttattagct tttcttaagc ttgactttag tatactccaa aatttgttaa     7500
gtgtcaacag ttttctttct aaaaaataaa aaaactttc aaaacgtgaa ataacgata      7560 taatattttt gttgtaatca atagaagaaa aggttgaaaa aaatgaacga aaacgaaatt    7620
aataaatttg ttgggaataa aataagatag cttagatttg aaagaggatt aactcaaaaa    7680
gaactcgctg aaaagaatag gtatgggaga cacaaccata gctaattacg aaatccatta    7740
tacccgccat tatgctaaat gtccgttgta gaggacataa aaaagaccc ccacaattaa     7800 gtgaggggtt ttgttatatc ttattaagtt tgaatccttg gatatatcga acgtgagcag    7860
ggtaagcctt actaacatgt tcaatttgaa taccagtata ttgttttttg ataaaatcaa    7920
cttctgcttt atcatttact ttgctataag ttccacggtc aaaatttagt aaaaggtaat    7980 cgccttttt atatccgttt aaatcttcat cgaatattaa tagccttgcg ctagtttgtt    8040
cattagatgc cactgattta gtctcctttg gttgcggttt aggtgtttct tttttttgtg    8100
tgccattgta atattgctta accttatcaa tatacgctgg tacgtccata gcttgtgggc    8160
atgccgttgc aaaaactgac ctatgaggta cgatagtttt attacttggt gcaattccta    8220
```

```
gacgtttaca aatttcagct actagcttag ccccagtctc aattgtttga gctgaaaaag    8280
tggaattttc tccattaatt ctattgttta catgttctac accgatacta ttttgattag    8340
tgattgctcc tgttcctcca caatgccacg ctgtgaagtt ttcgccaaca caacctacaa    8400
tttgattgtc atggataatg tactgtgcgc ttgcatctct tccgccaacg gtccatgtat    8460
caactgcatt ctgaaccgat aatccatacg ttccgtgtaa tacaatatat ttgattgctt    8520
tcatgtcacg ctctccccaa cttccaaata tttcagggcg tgagctagtg attaaacttg    8580
agtaaatatc tccattaaca ttttttaactc ccataggctc tcctttctta tcagttggta   8640
agtaaaaccca accaatgact ttaccgattt tgatgttagt tcctgataca aatagagaac   8700
catctgcata ccagtcgcgt ttaaccgctc ttactggtcc gccgacttga tactggtcat    8760
tgacaccgtc tgcattagta tctgtaaaac cgtctacatt ggcttctaaa ccaatgattt    8820
cagttccgtc actatctgtc gttgccatgc caatatgccc atagggatta ccctcagcag    8880
tggtatcaat aacataaaag gcggttgctt ttggagcttt gttaggtcca tccatttcta    8940
ctacaaaacc gtttgatttt gcttttttta aagcatcaat agcatttgta tatgatagat    9000
tcttatcagt aaaatgttgc acgattttat caactaacac aatacactgt gagccccact    9060
tgtttgtggg gactgtcaca aatgtattag tcagcgagtt tgcatagttt aaaatctcgc    9120
tgtttgttgt cataggctac tcctttggtt ttatataaga catagccatt gggctgtcag    9180
acaatccttt agtcgtaggg tctggtataa cgttgataat gtttaccaaa gtgataccaa    9240
ccacgtaagg atttgaaatg gcttttacaa gcaagtctgc aatagcttgc caagttgtta    9300
aatcttcagc ttttaatcca aaataagtta aaatgggaac aaaaatagct aggataaccc    9360
tagctaaaaa caatttattt tttgttgtga atcgcacttt ccagttaatt ttcatttttt    9420
gtcctccttt aatttaaata aagttttgat tgttcgtca tgagctataa cagtatcttg     9480
attaatttca actttgtcag ctaacttctc gtatttgttg cgcaagtctt tcctatctgc    9540
gtaagaatct tcccatctgt gctggttttc ttttaattca aaagctaatg tttgagtggt    9600
tgcttctaac aatttcattg tcgcttggtt ttcctcaagg gttttttgat tactttcaag    9660
cgaacgctga aaaggctcca acattcgtga ttgtagttta ctaaataacc cccaaatacc    9720
agtcagagct acacacaaag cgcctatttg caaaattaaa tccatacagc ctcctttcta    9780
atttgttcta ggcgtcaagc caaattcgag tttgagttga tttgcgtcgt aataggaatt    9840
aacatcattg ataatacgat ttgcaataaa gatattccca gccttaccga agtgctgatt    9900
accattattt aaatgtaatt cgggatgctc cgtaactgtt aaatcagaaa gattaataac    9960
gtttaaatca tactttgtag caatttcatt aattaccttg tttgtagcag aatatctcc   10020
accaaaaaca tggaaacaag tagaaatgtg aatggcaaca tctggattag cattttttat  10080
tgtttcaatc aatctgcaat agtaaccagt ttcggttgtt gcatactggt tataatcagt  10140
aaatgcatta acgtcagccg ccattgtatc ggttaaaccg ttgttagttc ctaaccaaat  10200
aaacaccgta tcatagtcgg caaaattata tttcggtaat tcatcagcga accacttaga  10260
tgggtaaatg ccagatacac cagcattttt tacttcattg ttcgtcatct tgccgacgta  10320
gtacggaacg ttttgattta tagaattacc actataaggt gcaattgaat aatagccgct  10380
tgtcagactg tcaccaatca ttagtgtttt cccaatagcg tatgagtaat taaaattagc  10440
agtgggagaa tcttttttggt ttagtgcatt gattacattt tgaaaagtat acccacctac 10500
aagcaaaaca tcggatggtg tcattctgta cattgaaaac gcaaagtact tggcatttac  10560
```

```
gggaatagtt attgttgatg gtattgaatt caaaccagaa ataaaagacc catttttcatc    10620 atagaaagca caccctgcat ctccattaaa tctacttgtc aatagcaatt cctttgcaaa    10680
cgagacatca attttatttg aacgataaaa tgccccgtt gcccaaacag tgaagtttcc     10740
gtttttataa tcaatatatc cgtcgtttgt caaagtaaaa gcaatctttt tgattgggtt    10800 tttatttca agataatata aacgattatt gataatatct gtaggaagca cgattttac     10860 ttttatcttt gaaatatcta agttataagc tgtgaatgca aaataatatg cgccattagg    10920
aaccattatt tcttctgaat aaacatttga ccctgaaata taattcccgg cattatcgta    10980
aaatgcataa ccatttgtac cgcccggggc aaactgactt gtcagaagaa tcttttttagc    11040 actaactact agaattttgt tcgaataatt gaaagcagta ttgttatatg cagtttcttt    11100
tccgtcgcta tattcgatat accctttatt tgtcaaaaca aaagatgctt ctatctcttc    11160
tgaaagagtt ttcccaatac tcctaatatg atcgccagct aacgaataaa ccttaccgtc    11220
gaagtcagtt ctagaatcaa caagttcaga cggtattgtt ccatcgccgg cacttgcgac    11280
aattgaactg attcgtgcat ttgtagaatc aatatctgca tcattagatg taatttgtgc    11340
ttgtagactt gaatctttgg catctagtcc gtccaatcgt acatctaaac tggatcgacc    11400
gcctcttgct tggatgattt ctgcatggtc agttaaagcg tttgagtaga tagaagccat    11460
tttatttagc aaatcaacaa cacttccgcc ttgtctattt aaatcactta gaatgccgtc    11520
tattgtcatg ttgacgtcat aatttggtat taagtcttta agatcgtaag caactgcccc    11580
agcctcaata gaaattaaac aacttctgtc agatgggaaa atgtagttgt caattttaat    11640
ttctagatag aaaactccag tttgtactgc tttttcaata ttaaatgtta ccgatgaatc    11700
tgatactaaa gttgttgatt gataaacgat attgttatca tcgcaaagtg taattgttgc    11760
tgtcttgctg tttaattcat ggtaataatt accttgttca tcagtaagcg taaaagtaaa    11820
ggtagaacca aagtcacctt gtttgacctt tgttccacct acttcttgtc ttaaatttaa    11880
tgtgttagtt aaaaatgtca tttatttcct ctctatgcta tccgtttcca tttgtaagtt    11940
gtcgggtctg aactattatc catagattcc caagttccgc ccattgatga agttggtgat    12000
tcattaactg tgctttgata tattgaacca atcggataaa acgtatctaa catgccagcg    12060
tttctatccg tccatatata atcatcgtaa ttggttgatt ggattgtccc agtataggtt    12120
ccttcatacc ttttattagt cgaattactt gtgctaaaac cagttgaacc atcagcacta    12180
tctgcccaag cttttccaaac tgtcaaacca tcacttccat cctcgccgtt gataccatcg    12240
atcacatttg taaatgtaat ctgcttagta gctactaact cactaccgac aaaggcatct    12300
actgtaataa ctagcgacgg attaacgtct gtaccattaa cagtataact atccccacta    12360
ttaagcagag catctccatt tctaaactgg taggtagctt caattcgttg agtgcctttc    12420
cacagataag caaataccgt tgatgttcca gtattgtttt taaaagttgt tgttccagca    12480
tttaaaacca aactgtatgg ttgaacagat tccgacaatt cagcgtaacg atcagtcaaa    12540
tctttactca acttattccg caatgctta taattatcaa aaattgtctg gttgcttgtt    12600
ggatttgtaa aactgatatg ttgttcggac actctagcag ttagcactaa tccgttttgg    12660
aagccctcat cgataacctt tacagtatcc ccgatatcta attcttcgga cgaacctttc    12720
acatcgtatg aaatggatgg gtagcagttt tttcttaatt cagccaacga acttgatatt    12780
aacaattcaa catctgttgt ttgtaattcc acggactttt taatccagtt atctcctacc    12840
tcctcacctg taaagctga tggatataaa tcccttgaaa gtggtgcgta cagcgaacca    12900 tttttttacat aaaaactcaac tacaccttct tcgttttcc actcacgata taaatcagtt   12960
```

```
ggtatgcgtg tgataacttc tttagattgt gtttctgtaa ttgttgatgg ttcattatta    13020
ccagtagaac ctgatggcgc tggtgcgctc tctgtgccat ctactcgctt accgtgtaca    13080
atttcaggcg gataacataa tgtttggata acgcctaaat attggcttgc actatatgtg    13140
cgttcttcta caaattggtg accagcatag ttttgttcca agactgtcaa tgtattgcct    13200
gacaagcctt tgataactac tgtatgtccc caaccaccag tccaaactgg tccgcctgca    13260
ttagctctga tatttgcgat agatcccggt attaagtgct taacctcgga tggtctaaca    13320
actttccaac caaattgtga ccaattgtaa tcctcaccga tatgtgaggc ggcagcaccc    13380
gcacctatta gccctttaaa tccgtttgtt acaccaccac ccaaccaagg accgccaatt    13440
gacatggcat accaagcact taatgcataa cattgaccag aaccaatacg agttcctttt    13500
ttagcagtaa gtgcattcaa cacgaaaata actttatctg cttttgact tactggcgca    13560 gtaccaactg tacctgctga ttttaattga gcatcgagag tatccatagc accattagaa    13620
ttactgttga taccaccacg gattgaccgc attaatggtg cataatgtgc atatcctgct    13680
gatgcataat cataagtagc accaccaact cggaatagac cttttgtata atcgtcaatg    13740
ttgttagcac ctttaacttt gtagattcct tgctctgcta ataaataagt gtagtcttta    13800
aagtagtccg acacgcttga gaaatgcatg taataaccgc cctcattggc aggtctagca    13860
gtaccttgag taactttaat accagatggg cgattacctg aaccagtcca agtaaggcca    13920
ccccagttat tatcagctct tgcgactggc gaattgcccc aaaaagattc taaatataac    13980
tgagagaata ctccagacgg taataactta tgttgaacac atagatttaa aatctcattt    14040
acaagacttt ttgaaatagt ccgacctgca tttgagattg aaccgccgtt atagttaaca    14100
gttctcaatt gtggcgctac atatttagga ttcgctttag ttacttttac atctacagtg    14160
gctcttccga ctggtgtgat catgttgaaa ataccagttt tgtctatttt tctagtaacg    14220
ccactgatgt tatacccata atgcaaccaa gcatcatctc tcttttttgcc aaccccttga    14280 ttcttgtcgt cattagcttt ataaatgttc ataataaacg atttcaagct agaatcttca    14340
tttagaatag tttcaaactc aatttcagca tcaaactgag tagcaataga taacaaacgc    14400
ttatgcttag tatctgttcc agtccattcc aacgttcgtt ctctatcttc aatttcatta    14460
tgaccaatcg taatagctcc accgataagt aagaagaatt tattacaata gtcaataaat    14520
gacatctcag ttttttgctgt aaatggacct gccatttcat ttagcaattc aagattgaga    14580
ttttcgcatt cacatcttat tgtattttcg ttttcctctg ttttcataac gctaaacaga    14640
taagtcttct tgtgatattt aaacgaaaca aaagaccttt cagacaaact ctgataggcc    14700 ttttcttta ctgtgtctga tttaatacca tttttataaa cagtgaactc aaatgttgat    14760
gatgcggttt ctaaatatct tttccaaata tcgtcataaa agaaagtgt atcttgcaat    14820 tcgttatcga cataagctat tttttgcaac ttagaatcgt gaataagtat atccaataat    14880
tacaaccacc tttcttcaaa tgctatttcg atatctggaa ttgattcatt ccatgacgac    14940
ctattaattt ctagtgtaga cttgccaact ggtattttta gccaatttga gccatcgaca    15000
acatgattaa gttttgcgat attatcaaca taaaatgttt tattttcgcc gtttataact    15060
actgtagaac ccttgccgta agggttaggg atattgtagt caaatgctac tttatctttt    15120
tgatacttaa taccatctag atacatacga gttacaatag gttttccgcc cattcctccc    15180
atgattacat gtagcttagc tgatttcttg tctttgagtt ctgaaaatgt cttaggaatc    15240
ctagatccca tccaataaag attgacttgg tcatcttgtc taacaatatc cgtccaccct    15300
```

```
ctgttgtcat taaatggatt gtctgaatct ttttcattcg ctttgaatgt tttttgaaaa    15360
tctgtgactt tataaccacc tttaccatct gtaaccataa agttgtgttc agtttcgtat    15420
ccaaattttc gcttgatagt ttccatccca tacaggaatt tgccttctgt gtcagaaact    15480
aaaattttga tatagccgaa ctggttaggg tcaccaatat gaaagatttg tctccaccag    15540
atgcgatcaa ataaagagcc atcacttggt aggtcaaaag ttaatgaacc gccgtgattc    15600
ccagatggta taacagttcc atctattgct aaatggtctc gttttaacca gtttataaca    15660
gagaaatttt tatctaagtt agttgttgaa tcgtttgaaa tagctacatt tttagcacct    15720
ttagtaaagc catcttttat acctgttcca ctatcagaat agtcaaaagg tctttctgaa    15780
aaacctcttg tttcactatc gataatctca cggtcaccaa tttccataac gccacttggg    15840
tttaccaatc caaatatcc attttcactg ttcattttcg cagtaattat gggataagtt    15900
ggaacgtttc cattattggt gatgttgaac actaactttt ctccactttc tgtgaagtct    15960 actactttt tgtaagttgt tgaatgtgcc acaccgtcag ggatgataaa ggtaataact    16020
cctttaccat ttagtctaaa ttcgtcgaag tctaaattac ccgttggaat cgcattaaag    16080
tatctatatg gttgatgact aaatttcaaa ggcttaggcg aatcgacata taaagctttt    16140
tgaaaattat cataatccac tagatttggg tattcaatat aaaaaggtac tttaataact    16200
ttttgcttat atctattatt cagaaaataa gtaccattta aactaacatc ttttgtattg    16260
acatcataat cagcaccacc gaaagaagta aaacccttta atatagttat ccaattcgtc    16320
aacttatacc cattgtattc tgcatcaatg gtcttataat tgttgctata taatctcatt    16380
aaagttctcc tttcgtccta gatagtgcat ttttttgttt cgtgatttct tcatcaactg    16440
gttgagcaat taatcgcgct gcttctcttt tatcgacttg tacagacact acaatctgtc    16500
tgtctttaat cccgtttata gcgttaaata atcgaaatt acttaattca ttttgggaac    16560
tgtttgataa ttgataagct aatctattac tagacaattg acctgatatt tggctttgca    16620
tatttactgg catatcagtt gcaagctgag gagttccaaa ggcgctttgc aattcatctg    16680
ccatacctga aacgctcgat ttgacgtttt taaagttatc ttttaaccct ttgtttaaac    16740
cgtccataat tgcattaccg tgtgggatca atagttttct atcgtactca ataggacctt    16800
tatgctctga aatccatgat gcgatgccac ctacaaagtt ttgaacttct tgatatttag    16860
atttcaatcc atctaaaaaa ccttggataa tcgctatacc agcttgcata aggttaacac    16920
ttgaaatctt acttataata gattgaccta attgaccaat ttcggatata actttcccaa    16980
ctgccgatgc aatacctttg acaagtgaaa tgataatttg aacaccagcg ttaattattt    17040
taggaaaatt actgattatt ccttgaagta aaattccaat aattttgata actgcatttg    17100
tgatatctgg taatctttga ataataccag ctactaattt accgataatt tcaacacctt    17160
tttttaaaac tgttggtaaa ttttgagata tcatatctat aaatttagaa atgacattaa    17220
ctgctgattg gataactgct ggtagatttg cgactatgcc atctactaat ctcaaaataa    17280
gatttgcccc agcttgcata ataactgggt aattttcata caaatactgt tgaaatgaaa    17340
taagaatgtt acctaagccc tcaattaatg aaggtaaagc ttgcataact ccaaccaata    17400
aattaccaat tagttcaccg ccttttgtga tgaaatttgg catttgtgca tccatttcac    17460
tgatcatctg tgggataagc tctgtaaatg caatttggaa catactccca ataccttga    17520 agatattacc gaccatcgga atgaaattac ctataaaaaa tgtataagta gtgttcgcca    17580
gttgctcaag agatggtctt atatcttctc caagcgctag tttcccaagt aagttacttg    17640
ctgatgcttt cattgcggac agtgatcctg agaaagtgtg ttctgcctct ttagcagttg    17700
```

```
ttccagtgat gcctatttct ttttgaactg cgtgaatagc tgaatagacg tctgacagat    17760
tgctcatatc atatttctta cctgtgagct tttcggcgtc cgttaagaga cgctccatct    17820
ccgattttgt gcctccataa cccaatttaa ggttatctaa ccgtttatac ccctgttttc    17880
acagtattta aaaagcctta taaataatat aagactttag ggactagact atatcttaa     17940 ctaaattgaa tatccagcct ttttgtttc ctttttgta ttcataattg tactttattt      18000
gagatttatg agtattgaaa aatttagcag tttcatttct ggaattaaaa ataatagttt    18060
tatcaagcgt ttcgttaaat gcagatattt tcttctgcct attttttact ctaccttcat   18120
atccatatcc ccaacaattt tcagaaacag ttacccatct taagttgtct gctctgttgt    18180
cggttttaat cccatttatg tggtcaactt gtggtaagtt ttttgtattt tttataaatg    18240
ctttcgctac taatctatga acatatagag gcgttgtttt tctgcctagc attatttgtt    18300
catatccact tgtgccaact cttaattttta aaattctacc agttttatcg tttctaattt   18360
ctccattttc gttatagag taattattac gttcttctat tattttccaa ttcataaaat    18420
gcctcctgat gttatcatta taacattttt aagacataaa cacaactata tacttaga     18480 caatttagtt agtacgcact tccattatcg tatcaataga taatgtactc ggtgacaaac    18540
cgatagtcgt ttgaccttcc tatttctagg cttggcacag gattgtcata ggtgttaccc    18600
cttagagttc ccctgttagc acatacttat ttttatttg tgtatgcaca cctctgatag     18660
agttcacgta cattcatctg cataatcact tacgcagcgg acattaaaca tttctgttct    18720
atcgtataat tctgcttggc gaaaccttga tatgcatatt ggatggattc cattgaagtc    18780
cattagtacg tccatttata tccaccggct gttctatcgt atttttattgc tctgcatatg   18840 ttagatttag aaatacctaa ctcattttga gcatcttcta acgattccca gcgttttata    18900
aaattcattt ttaagtcgta ttgggatact ggtcttctgt ttgtcgcctt tttccctttt    18960
ttagctttgg aaatattctt tctgtgttcc tctgtaaatt cgattccttt tttgccctcg    19020 gatatttttcc tagaccgttc ttctttattt atgttccaag attcagaaat cttctttta   19080 gtctcttcag aaagtttacc aacgctatca ccgccgttgt caatgttgta cccaaaaacc    19140
ctaacgttac tttgatagct gtttatcaaa tctatttctt tttgttcagc ttcttctttt    19200
gttagttttg aatacaatat ttcatggtaa aaagaatccc atccgtattt caatatcgca    19260
ttgtaaaaat atgcaacatg cgttggtttt ttaggtctgt accaggtgcc attgctgcgc    19320
catcttagtt caggttttct cccagtaatc ccaatataga ctttgttatt aatttttatta   19380 gtgtgtttat aaacagcata cattaaacca cctcgttatt ttagtttata gtattattat    19440
accataaact gataacccta acaagatggt tattgtaaca ttcacgctat ttcgctacta    19500
taacgccgtt ctcttatgaa ctgctcatag tttcctatga gtgtagacta tatcttctat    19560
gttgaccact tccactcgct tgagtgtacg ccttccggct agtcgttgaa ccttcccctg    19620 tttgggctt ggctgctgat tacccaatcg ttaaaatttt caaacattca cgcttatgct     19680
tatttcatca ttacgttgta gtttttaacg ctctaagggc cttccagcaa ttcaatcaat    19740
ttaacatgag cttttcaatg gaaaacccat cttgttacta ttatcagcca tgtcaaccat    19800
tgccatgtta gcaactttg cagccttaga agtatcacct cctagcgact gcaaaagact     19860
tgcggagaac cctgttacgt tctccatata tgcatttgca gacaatcctg ttgttctata    19920
tgcttcattc gcatatttct tgactgtgtc agcgttgttt ttgaataacg tctcgacacc    19980
acccatagat tgctgaagtg cggcaccttc tgttaatgaa gcttttattc caccaacaat    20040
```

```
catttcaccg attttagctg ccgctattat tgagctgata gctccaacta atttaccacc   20100
tattaaacta ccaacactgt tcccagcact tgacgcttct ggtgctaact gtttacttat   20160
cgaaccttga atacctttg cggacggcat aatttgcaca taggcttgac ctaattctgt   20220
tgccatttat tccctccttt ccttaacgaa ttttttcctt aattccatga aatcctcgcc   20280
agattcaaat gatgttaatt tctcttttgg ttttcattg actgattcaa taattgactt   20340
aggttgattg acacctttt gaccatcttt tgttttgac catagcaaaa tgcttaatct   20400
atctaacata ccagctagca tggtttgttc aatcgttaac ttttcctcag atatcgacat   20460
ccgtattctt gagttttctc tcaatcctac agaaaaaaca gctaccagat tcgctggtaa   20520
ctgtctatag tcgtatattt gataagtctc tgccaaatca caaataagag catcttcatc   20580
cttttttatc atctgggcga gggttactag tttttattg cttttgact ttcaaagatt   20640 tctgcaattt ctaggttgat tttttccaaa tctacaaggc cttcatcgtc tctgatatgg   20700
tcttttaatt tatcagcaag ttcgtctcca agcatgactt taacaagttt tggaagtaat   20760
agaggattag tgtcaacgtc tgctaacaat tcaactaatt catagttttt taatcgtgct   20820
tctgaaatct cataagcaaa tcccgatttt gttttccctg aaatcatact gtagtgcctc   20880
caatgtattc atagtgagtg ttaccgctag aatctggtaa tgcttggact gtaacttcat   20940
agccaaccgg ttcgccgtca acgtaagtaa tttcagccat ttctttaatt tttgcgactg   21000
gcaacacaat acgtttaaat ttgtcacgga caaccgtttc tacgacaata acgtgatcga   21060
ttttttcttt tgagttaacg gaaattttaa tacctgttgt aagtgttcca gttacattat   21120
cagccccata aacttccttg agtacttcaa tattgagtga ctcgataagt ttataagtaa   21180
atgtgtccga tgtcccagtt tgagctgtaa ggactgtatc accgcccat gctttaattt   21240 cttcggtatc tgttgtcatt tcgtttgtta aaccatcatc tgaaacgtag cctaaatcct   21300
taaatgccac gtctaaggct gttgttgcgt ctgcaggtag ctttgtccta agtggtgctg   21360
accaaattgc cccaccgact ttaggtttcc ctgctactac ttttgtagaa tctgtcatat   21420 cttttttct ccttaatagt gattaatgtc atataccgcc tgatagcgat attttttggt   21480
ttgtgtatcc gtgaaattgt agtcagaatt taacttaatc cctgatattt ctgggacttc   21540
aatcatagct tctacaactt ctttcacttg ttcgtttaat tctgccgatt cgaataaact   21600
atcggcgtaa gattgaaaag caaagacgga ggatttgagc ttgttaccct tgcctccgcc   21660
aattttttca atttgcacat actttcccctt aattccgttt tgatgctcaa aaaaagacgg   21720
tacatttaaa tgaccgtcaa gataattttt aataactaac tcaatcattt atgcaccgcc   21780
tttaataatg tattattttc agaattatct tttctagctt taaagctttc tgcttttacc   21840
atagcattcg cccgatttt accaacataa atatcttgct cgtatccatc gcctgccta   21900 tctttaatgg tagttgcatg ttcttttaag acagattgca tcgcttgcga tttcatcaat   21960
tcagcaacgc cagaacgatt aagtttaaat ataaatcac tcatatcgct caaccatcac   22020
tttcttgttc cattcaagcg gaattaagtc ttcaattcct tcaagtggca ttccaaccgt   22080
tcgccatttt tgaccaaaaa agataacttc tttatttccc caatcgtgca tatccccttt   22140
aggaagtgca agagtgtata ctgccttttt accagttaat gataattggt tagtgacatc   22200
atcagttgac gatggagaaa ctagcacgtt atcgactaga atctcaacat ctttaacaac   22260
tggtgttcca aacgggtcaa cagaaacaac ttgcttatca ataagggtaa tttgtattcc   22320
atgtatcttc cccatatata ttaatacccc ctattttttg tcgtttcaat cctaaccgtt   22380
tgagttctga atctttgata aagagtccac cgccggggct gaggtaagta cctgaccaag   22440
```

```
tgtatccgag tgctgattga cttctcttgaa ccattggttg accgctggta ggtgtcatta    22500
gtgttctagc gataatatca actgtaatag cttttaaaac acttgcgtaa gatacactat    22560
cagcgattga ctgatctaaa tctttaccga ctttttcagc ctctaaacgt aacgtgtcag    22620
agacgactgt taaaagcgcc tctgttcgtt tcgtttcgtc cgtcgtcaat gttctccaca    22680
aagcagtaac atctgcgacc gttgcaaaat tagccatcat aacctcctaa tataaggcta    22740
tttagcctct tctttctttt tcttaactgt ctcttttacg agttcccaat caccaactaa    22800
agcagaatct gttacgacta ctgccccagt gttttatct ttgtaaattg ccataaattc    22860
ctcctaaaat taagctcgga cttctacacg agcgaatgct ttttcatcaa ggattcccca    22920
tccaataaac gcttcagaac gtagtaaaat ttcgttgtac gctttaaggt cacgaccaga    22980
accgtctgga tcaccatatt caataatttc aagtggaata ttttcagcat aaccccattt    23040
gaatttactt tggaagtcac ctacgatagc gtggtctgtt ttagcagttc caccaactgt    23100
tgtaagtgtt ttgttcatgt caagcttcat attaaagaag ttgtctggac gttgcccaaa    23160
gcggaattct ggatatgctg ggactttgtc agcaccaagt tttactttag acatatcttg    23220
acctgcttga ggcgatagag caataccagt tacttcattg ccattaacta caatagtgtt    23280
aaccgcagca tcaatattgt catcaatagt tgcggcagta taaggcacaa cattacctgt    23340
aatgacaccg tcaaatgagt tagtcgcttt aaatgtagca tccgttaaag aacgtggttc    23400 taaccgtgg atcgctgcaa tatcaaatgc ctctgccatt tttttagcaa agccctctgc    23460
ataatgtttc aagaagttta agcgtttctc ttcagatgca tatttaaatt catctgtcat    23520
acgtgcttga taaacaaatt tcatcggctt aatgatttta gatgttactg ttgctgttga    23580
gcttaatttt tgttcaccct caccaacgat ttgagcgttt ccgtctaagt tgaaaataaa    23640
ttgctcaact ccattgaatg ggattggtct ttgacctgat aattttgcaa gcgtagaatg    23700
tccctgcaca ttgctcatga tttctgttac taattctggt ttaaatagtg ttcctgcttt    23760
aattgtgtct gccatgtttt ttaatctcct gtattaatta agtttcgtgc catttctgcc    23820
caatttgctt cttttttgtc agcgatggct ggttcgtttg attttaaagg tggtgttggt    23880
tgcttaggtg ccaaataact tgctagtcgt tcagcatcag ctttaaaccc atcttcatcg    23940
tcgccctgta gtcgttcggc taagtcaagc ggtaatccat attctgttgc aatgcgttgc    24000
ttagcggttt gtaatctagt ttgagttaag tctccattta atgattcaac ctgagagctt    24060
aattctgttt ctctagtttt taaatcatta attgtatttt ggtaagttgt ttctttagct    24120
tcaaaatcag ctaattgttt tttcaagtct tcataatctg catatttctc acgctctcta    24180
gataagcgtg ttttaataac tgcatctaat tcttcttgag tttcaataat tttaaaatct    24240
gacatgtaac gtcctttctc ctgctttgcc ctgcagttcg gtaattttg cattaaaaaa    24300 agacctgttg gtctcttaat aactaattct ttgctttctt ttaggcttgg ttgttgcaca    24360
aagccagtgc gctagcaatg cactatccat tagactaata tctctatcat caaagagcga    24420
cttgtaacca aaaccaccat tagaacctat gttgcgtttt gaacagttgg ttgttacagc    24480
ggtaagggat ggttggttat tatgtctcaa agtaccttga gcgatagctt gttcccacat    24540
tgcgttagct gttacgacct ctgcaactgt tggaagaacc ggagctttaa gtctgaaatc    24600
tttcatttct gcttctagta ttcgttgacc gtttgcacca tccacgacta ctttctcgac    24660
gtcagcattt tgtaagaaat tgattatcca ttgtgagccg tttctaatcg atacacagtc    24720
aatagtttca acaaagactt tttcatcttt ggttttgact gcgattgaca tcgaaacatt    24780
```

```
atttccatct tgtccgtatt taactgcaac aaagagctta ctgttaaatt ctggtatttc   24840
ttcaatttca agtgcagacc aatcttttc tgatatctcc gatttcatat tgaacgtagg    24900
ccaatagcct agacgttgaa tattgtggtc aagcccattt tccccaagct ctgcttcaat   24960
tttacgttcg tttaagtggt acccaattga tggattagtt agataccaac tgtctgtgtc   25020
gtggatatcc tttacagcat ctactgacca ctcagcccaa ccagaatact ttttattgcc   25080
ttttaaaaca tctttacgat aattttcaaa gacggtacca gttgaaactt cagttggtgg   25140
tgtacctaac ataattgtca tagggttgtc actgtcggaa acggtatatt ttaaagctgt   25200
ttcttgctcg actgtgtact cttgcgcttc gtcaattaca agtaagtcaa acccttcacc   25260
aaggccaccg ttagatgtcc ttgttcggaa ttggatgaca gaacctgttg atttaaattc   25320
aatacgttcc tgccctttg ctttattgga agtgaagtct tcgccatcga catacccaga    25380
catttcaagg tattttttta gctttaagaa cgatgaatgc gatgtactaa ttctatgtgc   25440
cgtgtgcaac atatttaaat tattatgcag tccccataat tcccaaagat agacaacttc   25500
cgttttaccg ttacgacgag gaagtgagta cccatatttt tgatgtaccc acaaatcatc   25560
atcgttgaca gccatcatgt cttctagtag atatttctgc cagtcgtagt atttaagccc   25620
agtctttgca taataaccaa gcgcctcagg tgatagtgat ttagtccaat gtaaatttac   25680
cgattgagtt ggatgttgat tgccaagttt ttctttagtt ttgaccatca catgtttcct   25740
ttcaatcgtt attgcatgat aaccctgtcg ctgggagatg ttagatcact tcctttcgaa   25800
aaatgcgatt cttatccctt ttaaaattgc cattaatgtt gctagtaata acaagcaaat   25860
aataatgcca aatagatata cagcaaattg ccaaaaaatc atctcacccc tccacactcg   25920
atattgagca atctttattt aaatcacgtt ctataatcgt tatcgttctg tcttctttt    25980 cgtattgctc taagtcgtca tcaaaaatct ttttgcaata tctataacct tgctatcga    26040 taaattctcg tgcatcatct aagttgtcat aaacacctaa aatgtgtgtg tagctacatt   26100
cataatcaaa tttgaaaaac tctaaaatat atagtttcat atctcacctc cacccttcg    26160 tataagcatt ctgaatacct cgtccatctt ttggatggta ttccacgaca cagtcacaat   26220
tttcatgcct tgcgtagatt tctttatcca ctgggtaatc ataagttcca gctaagttct   26280
cacaccattg gcaacattta ccaatcacat atctagttag ttttggtttt aaaccagcct   26340
ttgcgtgaaa atcagcattt gtcataataa aatcatctat aactgactgt gagaaattga   26400
caactgggtc ttttaatatc catttgactt catcaaaatt ttcttctaca gataatctgt   26460
taactatgcc atcgactta tcttgattga ttttatttgt ttttggtttt aatccgatgc    26520
cagcttcttt atttaaagcg gtttgtaact caaccgcata atcagtaact aatttatgat   26580
tatttccaag cgtctcattt aatatccttt ctgcgtatat aaaaaacatc ttaccatcag   26640
gcaaaatgct tgctgataat ttactatcaa aaacctccga taaaatattt ccaacttctt   26700
gggcgtatag ataagcgttg gcgtgattct tagcctctag caacttaggt atttttttat   26760
tactcttgta cttgctcgaa aattctttt ttaaatcatc taataattt ggaacaatat     26820 catcaaccat ctatgccacc gtcctttatg ccagttgttt ggaataatac ttcgccaatg   26880
tttaattctg ggtaagcttg tgaaatcttg attagaccat ctccaattgt tgaaagacta   26940
gctccatcaa tttcaaacaa tggttcccaa atgatttag tattcataaa cattgtgcgt    27000
tcatatggtt ggttatcacg taaacaaact gctatataag caacatttag aaaaccgcta   27060
gcgaacgacc gttgggcttt tttagcagat gcacgtaaat tttcatggct tgccttaata   27120
gcctcaacgc ttgaaggatt atcagacgga aagcctaagt catctaatgt tagcccagag   27180
```

```
ccacctgcga ataatgaagc atacattttt aattgactaa agaatggctc catgcttgct   27240
gatgcaaatt gaccgacaac tggtttatcg ttgtcatcgt ctttggtgat ttctaaaaca   27300
gttgaaactg tcgctttcca cttatccaat gcctctgcgt cttgacttgt tcccaaaacg   27360 tattttgtg ggaatgaata aaactctgcg gttgcctcag cacgttccaa tgtccgttta   27420
gcagcctttt gctgatacat gcctgaccgt gtgattcgac tacggccaaa tggtcttact   27480
gcatctggtc tatgaataat cggtactagt aaaggttggt tagttggatt tgaaatgcta   27540
taaggctcac catcactagg atagtaccat gtttctgttg gcgtgaagta tgcctccaaa   27600
ataggattat cgttctgatc aacttctaag actgcatacc cttcagttaa taggaaagta   27660
gtaggatcta aaataccagt tgccttactt gcttcaatga cttgtaagcg tggaatttta   27720
tcaccgtctt ttgaaatata aacgaatgca catgagccaa tcaatgctga ttgaattgca   27780
gtgtcaaaaa agatgtctgg attatttgca ttgaatattt ctgttgcatt aaaatcatca   27840
ttcccgaatt cacggaaaac aattctgtca gacagtgcat ccactccttt ggtagtccat   27900
tctaagactg accgataagc acttttaacg ttatacggca tgacaatact cattgtgtta   27960
tcaatgtcct gcattgcgta ataacgatag cgttttcaa cacccatttt ataaagcgct   28020
agctttctac gtaggaagtt cattccagtt tgtttcattt gattttctcc attattaatt   28080
tttcaaaatt aggatcgtgg atatctattc cctcgattaa tatccgacca acataaccaa   28140
attgcttttc attttctaaa agctcttgtt ttttcttttg gtaatatttt tcaatatcac   28200
gtattttttt aggtttagta gagttttcaa tgttagtttt taactctgcc tctttacgtt   28260 cttttcctc tttccgcttt tgcgcatta agagtttctg cttttctgaa atgcctattt   28320
ttcggcattc ttcactacag taagttgcac gatttgaagt tgtctcaaat gactttccac   28380
atgttgcaca tattttttc attatctctc caatctaaat cctaacgtga ataaaatgt    28440 acaatacagc gggaaggtct ttcgctccct gtttaaggga ggatatgcgc catatttatt   28500
ttaggaatgt tttatttcta aaaatatctt tatccctctt taacgtatta caatagtgat   28560
gagccaagtt aacattatcc caagaatgta aaccacctt tgaaatagaa atgcatgct    28620 caattgatgg ataagtcttg ccgactattg tataaccttc ttctgttatt accttgtcat   28680
cgaagtcaca ctctttacca catagatagc atacaccatc gtacttttta aatagcttct   28740
gtacggtaat atctttatcc acaatgttag attcattcaa gcgattcgaa ttatacaact   28800
tctgcattct gttggctctg cgttactac atagtggggt gcaagttaaa gcttggggca    28860
gtatattata gaatggggta ccgcattcga cacagggtct ggttagttca actacctttt   28920
ccattcttaa tacctcttta tttaacaact tagctatatt agaaatggct ctttgttttt   28980
gtctttcctt ggcttcgatt tctaatctag caagtctctg ttttctttgt tcgcctacta   29040
ttgctaagtg tttctctaga ggtttgtgac ctctccttct atcttcatat ctatgtctgc   29100
atgaagcacc acaataaagt gcatttattt tcatatgact tatgtctgcg ttacactctt   29160
tacaattcct aatgtcctcg taatcatatt taccgcataa cccgttttct tttctccatc   29220
tttctctgtt tcttttttctt ctaacttctt gtttacatgt ttcagagcaa tacatagtgc   29280
ccgctccgtt gacatgcatt tcaaattctt tattacattg tttgcattgt ttcattggaa   29340
caccaaaaaa agaactgcca aaacagttct cctctttcta tttagttatt tgctcgtata   29400
atgcgttcta agagcgttta gattattgtg gtacatttac attgcttcac attttaaact   29460
cgtaggacgt ccattctatc gtcttaggaa gatttctgtt accaatcgtt tcagttgtgt   29520
```

```
tcgtttgtcc actgtaaagt ttatctgact tgtccctgtt acatttccaa tgtgtcaatt   29580
gtaagttgtc catgtttgat ggatttccac ctttagaaac tggaatgata tgatcaattg   29640
ctggagacag tggatgcgga taagcaagcg tcttgtccac gtcttgacca cagatgccac   29700
aggtgtgttt agtctttagt agccgtttct tattccgttc aaatgccaca cggtgggggc   29760
cttttttatc tagcctttca attgccatat gggggcctt tctaaatata ataaaaagcc    29820
actcaatgag tgactaattg gttaaccatt gataaatagc gaatgattgc taagcctatt   29880
gcctacccca ttctgggaca cttctattta tcttatagga acagtcggaa tcgaaccgac   29940
ctcaaactaa cccaagagta ttcccacaga taataggtgt acagtctatt atctaattat   30000
gcaagagcgt accttgcaaa tatgatagca ccactatcac atttatgatt tgtcagcgta   30060
actaatcgaa ccgtttaact atatcgtggg ccacacgctt gtaggtctct gagttgatat   30120
agcatggtag aaaaccaac acgtcagtac gtaactgcct ttcggaatgt tgggtagctc     30180
tttcgagcag acaaccattg cacgaatcga acgtgcgtcg ccagtatggt tactttttt    30240 tggaaggagg atacggaatc ctattacaat ttttgtttta gtagcagtaa cggcctgcaa   30300
acctacacta ctaattgagc ccgtaggatt cgaacctaac cacaatagaa gttcctatag   30360
catctattgt ccaccaacct catggctcac cagtatttct tttttcgtgt cgctaccaaa   30420
cgacaacatc aacttcaaaa tagtaagttc gatttattta taagtaatcg tctaatcata   30480
tgtagaccag tttgttaatt gttatctctt cttgctattt cgataatact ataatactac   30540
tttacaaagt ataatgggtt atattttatt ataaataata ctattctatt attttgtagt   30600
ctaaataagt atatttaatt tttctatcgc ttttctttg atagtaaagt attttgcttt    30660
gctcattttc aaactatcac aagcatcatc aaacgtttcg caattaacat atcctgctaa   30720
caatacattc tgatgttctt tatcttccaa ttgataaatc atctttagta tttctgattt   30780
tcgtttgaga ttcttttgta tttgttcaat ttgagtatcg catctatcaa tgatagctac   30840
attcttgtca gtctgtgact gcttgattcc gccagatact ttcatatcat tccattgagg   30900
actacttaag acagaacctc tagtagcctc tatatctttt tcaagttcaa ttgtatttgt   30960
tttaattgcc tttaattctt ttaacaacat atcagctttc gtctgatttc gccccattcc   31020
aagtctcctt atggtataat atagttacga actaatacca aggcgctctt tcgtggggcg   31080 cttttgttg tctatcgaa acctctcttt tatttatttt tggacaggca cacgatccgc     31140
attgaaattc tcacgatgcc ttatttaata actggtaacc gataaccagc tttagattag   31200
tatttattac gtaaggagac ctccatttt taatttcggt taataccaac cgagcgagtc    31260
gaacgctcgt gataccgttg ttggttattt cagttgcatg atcatatcga tatgtgggc    31320 aaggattggt tgtaaaacag gaactaaaaa cgaaactgca atgaatacga tgccaattaa   31380
taaaagagtc aaggctaatt ttatttttc gccatcctcg tctgcagcaa ctgctactat    31440
aaatgctgct ataataaaac ttcctaagat ccacactgaa tcaatagcac ttaacactct   31500
atatacttgc cattcatgta acaaccgctc ataaatctgt ggtgcattca tattcagact   31560
gcttacaatt ttctctagtt cactagctga tatatctaaa atcttcgcta gtggtttaat   31620
tagttcgttc actcctctac ctcctcaatt tcaaaccaat gtttattccc accgtagtca   31680
atccgtgtaa cgttttttgtc ctctactggg tcaaatccat gtgcaccaaa tttaaactcg  31740
ttaaggcaca cgtcatggaa tccttggatt gcttgctcct tagttcaaa gctacctttt    31800 aatatgcgtt ctgcatcgtc acaataatat aagttgtatg tcataattcc ctcactgata   31860
cccatacata atctggataa ttcttcattg aattttcttt gctaatcaat aagtcgcgtt   31920
```

```
gataattgtg attattcatc agaatttcac tagctagtgt tttcggcacc tcaattgtag   31980
gtggtcctac tttctgaccg tttacatatt cttttaggtt tttaaacgta taatcagttt   32040
ctgtttcgct gactattact gctcctaccc aatctggttc gttcatttca actcctccaa   32100
actaacccac ttaaactgtg gaaaccgttc tgcttctttg cgtgttaata acatagcatt   32160
gttaaaatca tctactccaa aacataaacc gcttttgta tcaatgtcta catactgtcc   32220
atttatactt ttcaacactc ctaattcttc agtcatttgt tacctcgctt aaaatcgcaa   32280
tagctttctc atatttgtca atcaataact ttgcattgtc catatcctca aaacgatttt   32340
cattataaaa actcttaaa aaatctaaat tatcctctag cgcttcgatt ggaagctgta   32400
attcttcagt gttaattaat tcaggcatgt tttatccccc atttcctgtc aactcagcaa   32460
ttctcgcagt cttatcagct gattcttcac ttactttttt aagctgatac tgcgttctgt   32520
ctagttgacc agtaagtcct ttgatttgtt ggtcttttga tttgagttct gttttgagtt   32580
ggttattacg ttgttttaat tgattatttt ctttattaac aatactgcaa gcgagcataa   32640
tgccaataag aagtcctaat aaaataaggt tgagccacaa caaaaaatca ttcttcattc   32700
ttccacgctt tctagtaagt cactgtttg ataaataaag ctatacccaa atactttatt   32760
acgtctgcct gcaaggcatt cagaaatatt tccattagac ttcatattta aaaaatattg   32820
agcgtctttt atactttga attttccgtc ttttaacatt agtattggtt ttttgttctt   32880
atctgctttt tttgatactg ctactacttc tttatccatc actctttaac ccatttcaac   32940
acaacgtctc cttcttttc atacgtatct acccatcgct gctcaccatc ggaaaagata   33000 cataaccta acggataacc catttcatca aattggatta catttgaacg tatttttatt   33060
ctcggtatat ccttctttt gaagaacatc attccacttc ctccaaaaat tctaaatagc   33120
gtgggtcaat agctttaact tctgctcgtg tgaatttggt tttgtcaaat tcatcataag   33180
tgtttgatag aaaatgtgtt ccatctcttt tgtcaatatt taaatatcca ttctcaccac   33240
tcattaaatg tacataatac aaaggctctt ccacttccca tttaccatca aggatggctt   33300
ggtttacttt tagttttaat tcgctagtgt taaatattct gtttaattca ccatctgaat   33360
tatataaaag ctttattaca ttttgtttta aatcatcatc attaatcgta aatttcttta   33420
ataattcatt ttcttctctt gttaacttaa tcatttaaaa cctctatatc gtatctattc   33480
ttattagaaa agttcagtaa taaatctaca atttctccgt gagccattac ccaaaaatca   33540
tcatttctgt atttgatttc ataaacgtca taatcattcc atttacaatc agtgattttt   33600
acaatgtcac cgtctttgat ttcttgatta tttatatctt taaaaatcat ttaatcaccc   33660
cacacatcat taatattagt attactgtta aaatcgcaaa gattgccagt agtaaataaa   33720
ttaaaatcat tcttctaccc cttaatttct actaaatggc tatcacaatc ctctgtgtaa   33780
gaaatcaatt gaatagcttt acgtgaatta atccaaccgt ttttatcttc gtagtcatct   33840 gttttttga ctgttccgaa ttgacgtaaa ataacaccat tttcgtctac ttcttttca   33900 aatgtatgcc tgtgccctgt gtgaacttct cttactttg ttgtaaagaa aatatcttca   33960
aattcagtcg caaatttcat tggaagttct tttaatttaa cggtatgacc gtgcgataac   34020
atcactccta taggtcctac cttataagcc attctccatc tattatgatt gtttagctta   34080
acatctggat acttagccat tagatactca ttaaatacat attcaagctc tgaatgattg   34140
ccaatagcat attcaaacct aacttcattt gagttactca aggcagtcgt tataatctca   34200
ttgaaaaaag ttttagcatc ttgtacagct tgtggcatat tgactgtttc taattgtgtg   34260
```

```
cctcttaccg tagaagatga tgtcataaat gcactatgga ataagtctcc tagttgctcg    34320
ataacaattg tattaaaccc atttcgaata aactctttaa tttttcagt tttaacttct     34380 aagtgttcaa ttttagtaac cccaaaatgt aagtcggcaa gcgggataat taagatatct    34440
tttccgctat ttaatttaac tggttttatt ggttttactt taccagccaa taaatcagtt    34500
aatttatttg ttgacatttt agttcttggt cttactgtga tagttgattg ataattataa    34560
aatgcactac cttcaagagg cgttgtccat tcatttgatt taccagaaac gatttcccag    34620
tcatctggat caaaaccatg taaggataat agttgctctt cagttaaaag ttgaccttcg    34680
cttaacttta attttattga gtgtgtgagt gatttttttcc cattcctatg catgtcatat    34740
tgactaagtg tcttgtggct acctttaatc cgtttaaatt ctgcatacca gtctgaattt    34800 tcttttttttc ggcaatagct tcttaagtca tcgcctttgt aatggtcagg ttatcaagt    34860 ttatttaact ctttagtcct attttcccaa ctcaaatcaa agtagtttct taaaatgtaa    34920
attacgtttt cttggttaaa ctgtttagcc attcttaccc tccaaccaga ctgctaacat    34980
aaggcaatag ttagccatgt ctttaagagt gtctgatttg ctttctaata cttgattttt    35040
attcttggta agattaacca accgttggta cttatcgctt atacggacga ttccagccac    35100
ctctccgaac tgttcaagcg attcttcaaa ggaactccca taatctgcat tcttcttcaa    35160
aaacgtttga aaattttcgt catatacttt ttgcattgct tctgcgttta tcttatccat    35220
tcatcacctc ttttaattgt tgaatgatat acttgatttc ttcctttaca taattaatat    35280
ctctgtattc cccataaggc gaaacagggg tccaatccca tccgtgcgca cagtcgaagc    35340
caatatagta tccatttgtc ggaaaatact taacgccccc agcgttaaat gtaattccac    35400
cgtggcactc gatttcattt tcgtctatta gaccgactat attttcagga acttctacat    35460
atccacataa atgccatcct tgtatcatta cgatgactgc attataacca tcaataacta    35520
tgtttaattg accgttttta cctaatattt ctaagtctcg tttgtataat tcattatcca    35580
ttcgctaacc ccctcataat aattttttgcc tgtccttcag ttggtgtctt tgcacgtaac    35640 caaaacttttt tgattaatcg ctcttccatt ttcaaacggt cagccatttc ttcaattgat    35700
aatttgttat ctgtcatata cttaattaag taatcggcaa catcaagtgg caacatgcta    35760
tcatgtgatt taattgcgtg cttgataatt aatacatttt gtctttgttt tctcatctta    35820
ttaacctgct ttcttccaaa gccatttttt taagtatctc tctatatctc tgtcttgata    35880
ctccatggcg tcttgcttta tattcttccc attccagttc cacttcctca gttttatgtt    35940
cgttttggtt ataggaatgt ttcataaatt cataaaataa atctttatcg ttaaaataat    36000
tttcaaaatg ttttaaatat tttattggtg gaataacacg ccttggtttt aaatttgata    36060
ctgatttata aaatctctca aattcttctt ctcccatctc tggtaccata cctcttaaaa    36120
aatttttgta ctcccttggc atgttttttgt aaaatctgtc ttcaattgtc acttattatc    36180
ctcaatgcat cttccacaga cctagccact ccagctagtg cgcctcgttt tgcatactt    36240 tctataaata ttttctgttc tggtcttaat tttccagttt catttttttac ttcgatgaag    36300 aatgcctttg catctccttt acggaatcca gataaatcac aatatccttt aggcacacca    36360
gtttcaaacc atctgccatt ttgcatttta actttaccga cgtttattct aaatactgta    36420
tgacctgctt ttgataaacc aactctgatt tgattttgga ttgtgtgttc ttgtgtcatg    36480
ttcctcctaa aagttaatgg tactattaac cacctataaa gtcagtcata ccaagtgatt    36540
agaccattat ttttaaaaaa agttaaaggt taatagtctt tttatactta tatat          36595
```